United States Patent [19]

Liesch et al.

[11] Patent Number: 5,712,109
[45] Date of Patent: Jan. 27, 1998

[54] **ANTIFUNGAL AGENT PRODUCED BY *ARTHRINIUM ARUNDINIS* ATCC 74359**

[75] Inventors: Jerrold M. Liesch, Princeton Junction; Maria S. Meinz, Fair Haven; Janet C. Onishi, Westfield; Robert E. Schwartz, Scotch Plains; Gerald F. Bills, Clark; Robert A. Giacobbe, Lavallette; Deborah L. Zink, Manalapan, all of N.J.; Angeles Cabello, Madrid, Spain; Maria T. Diez, Madrid, Spain; Isabella Martin, Madrid, Spain; Fernando Pelaez, Madrid, Spain; Francisca Vicente, Madrid, Spain

[73] Assignee: Merck & Co., Inc., Rahway, N.J.

[21] Appl. No.: 789,348

[22] Filed: Jan. 27, 1997

Related U.S. Application Data

[60] Provisional application No. 60/010,932, Jan. 31, 1996.

[51] Int. Cl.$^6$ .................... C12P 33/00; C12N 1/14; A61K 31/56; C07J 9/00
[52] U.S. Cl. .................... 435/52; 435/254.1; 514/182; 552/540
[58] Field of Search ............... 552/610, 540, 552/623, 627, 632, 633, 635, 650, 652; 435/52, 254.1, 256.8; 514/182, 169

[56] References Cited

U.S. PATENT DOCUMENTS

| | | | |
|---|---|---|---|
| 4,781,727 | 11/1988 | Burg et al. | 514/172 |
| 5,023,250 | 6/1991 | Adams et al. | 514/179 |
| 5,198,432 | 3/1993 | Fariss | 514/182 |

OTHER PUBLICATIONS

De Bernardi et al. "Fungal Metabolites XIII: New Cytotoxic Triterpene From Hebeloma Species (Basidiomycetes)", Tetrahedron Lett. (1983) 24(15): 1635–1638.

De Bernardi et al. "Fungal Metabolites. IX. Triterpenes From *Naematoloma sublateritium*", J. Nat. Prod. Chem. (1981) 44(3): 245–376.

Tsuyoshi et al. "Novel Triterpeneoids from the Fungus *Ganoderma licidum*", Agric. Biol. Chem. (1988) 52(2): 367–372.

*Primary Examiner*—Jon P. Weber
*Assistant Examiner*—Susan Hanley
*Attorney, Agent, or Firm*—Elliott Korsen; Mark R. Daniel

[57] ABSTRACT

There is disclosed a compound having the formula

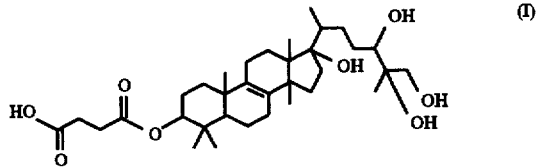

which is produced by the fungus, *Arthrinium arundinis* ATCC 74359, and exhibits antifungal activity.

6 Claims, No Drawings

ANTIFUNGAL AGENT PRODUCED BY *ARTHRINIUM ARUNDINIS* ATCC 74359

This application is a continuation of the U.S. Provisional Patent Application 60/010,932, filed Jan. 31, 1996.

BACKGROUND OF THE INVENTION

The present invention relates to a novel antifungal compound, compositions and methods of use. The compound and compositions exhibit broad spectrum antifungal activity against human fungal pathogens.

Clinical treatment of human fungal infections has relied mainly on two types of antifungal agents. These agents are amphotericin B, flucytosine and nystatin, which are fungicidal and capable of curing fungal infections at the cost of severe side effects to the patient, and fluconazole and other azole agents, which exhibit fewer side effects but are only fungistatic.

Thus, there is a need for new human antifungal agents.

SUMMARY OF THE INVENTION

The present invention is directed to the compound of the formula (I):

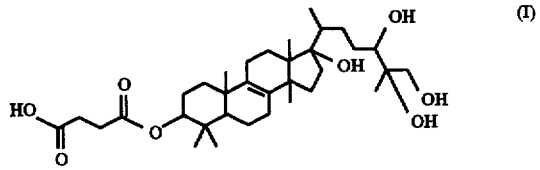

The compound has antimicrobial and fungicidal properties and may be useful for controlling systemic and superficial fungal infections in humans with fewer side effects than standard antifungal agents such as amphotericin B or fluconazole.

The compound is obtained by cultivation of a strain of the fungus, *Arthrinium arundinis*, MF 6175, in the culture collection of Merck & Co., Inc., Rahway, N.J.

DETAILED DESCRIPTION OF THE INVENTION

The compound is white and characterized by the following spectral properties:

Infrared Spectral Data

Recorded as a thin film on ZnSe: 3200–3600, 2940, 1710 $cm^{-1}$

Mass Spectral Data

Mass spectra were recorded on JEOL SX-102A (Electron Impact, EI, 90 eV), JEOL HX110 (Fast Atom Bombardment, FAB), and TSQ70B (LC/MS-ESI, Liquid Chromatography-Electrospray Ionization) mass spectrometers. The FAB spectrum was am in a matrix of dithiothreitol-dithioerythritol (20/80). The exact mass measurements were made at high resolution with Ultramark™ 1960 (Fomblin) as the reference compound.

The molecular weight 592 was determined by negative ion ESI in a solvent system employing dilute trifluoroacetic acid (TFA) (observed m/z 705 for [M+114 (TFA)–H]⁻ and m/z 1297 for [2M+114 (TFA)–H]⁻. The highest mass ions observed under EI and FAB corresponded to loss of water from the molecular ion.

HREI-MS Found for $C_{34}H_{56}O_8$—$H_2O$: 574.3830; Calculated for $C_{34}H_{56}O_8$—$H_2O$: 574.3869

NMR Spectral Data

NMR spectra were recorded in $CD_3OD$ at 500 MHz ($^1H$) or 125 MHz ($^{13}C$). Chemical shifts are reported downfield from TMS (tetramethylsilane) and spectra were referenced to the solvent peak (3.30 ppm for $^1H$ spectra and 49.0 ppm for $^{13}C$ spectra).

$^1H$ NMR SPECTRA $^1H$ NMR: 0.86 3H s, 0.88 3H s, 0.94 3H s, 0.97 3H d (J=6.5), 1.04 3H s, 1.08 1H m, 1.11 3H s, 1.16 1H m, 1.22 3H s, 1.37 1H m, 1.50 2H m, 1.51 1H m, 1.54 1H m, 1.55 1H m, 1.63 1H m, 1:63 1H m, 1.66 1H m, 1.71 1H m, 1.73 IH m, 1.87 1H m, 1.92 1H m, 2.00 1H m, 2.05 1H m, 2.05 1H m, 2.08 2H m, 2.18 1H m, 2.22 1H m, 2.59 2H m, 2.59 2Hm, 3.43 1H dd (J=10.0,1.8)3.46 1H d (J=11), 3.52 1H d (J=11), 4.65 1H dd (J=1.5, 2.5).

$^{13}C$ NMR SPECTRA $^{13}C$ NMR: 15.1, 19.1, 19.2, 19.3, 20.5, 21.9, 22.3, 24.2, 26.5, 26.7, 27.1, 28.3, 29.8, 30.4, 31.0, 31.2, 32.0, 32.6, 37.8, 38.0, 40.0, 44.2, 46.8, 51.1, 51.4, 68.3, 75.7, 77.5, 79.8, 87.2, 135.4, 137.0, 173.8, 175.9.

The compound of this invention has antimicrobial properties and is especially useful as an antifungal agent against both filamentous fungi and yeasts. It is useful against organisms causing systemic human pathogenic mycotic infections such as *Candida albicans*, *Candida tropicalis*, *Candida guillermondii*, *Candida glabrata*, *Aspergillus fumigatus*, *Candida pseudotropicalis*, *Saccharomyces cerevisiae*, *Aspergillus flavus* et al. It is also useful against organisms causing superficial fungal infections such as *Trichoderma* sp. and *Candida* sp. These properties may be effectively utilized by administering compositions containing an antifungal amount of the compound to an area, object or subject, on or in which fungi are to be controlled. Thus, compositions containing an antifungally effective amount of the compound and their use for the control of fungi are aspects of the present invention. An especially preferred aspect of the present invention are compositions in a pharmaceutically acceptable carrier and their use for the control of mycotic infections by administering a therapeutically effective amount of one or both of the compounds.

The compound of the present invention is a natural product produced from a strain of *Arthrinium arundinis*, MF 6175 in the culture collection of Merck & Co., Inc., Rahway, N.J., which has been deposited under the Budapest Treaty in the culture collection of the American Type Culture Collection on Jan. 23, 1996 at 12301 Parklawn Drive, Rockville, Md. 20852 and assigned accession number ATCC 74359.

The producing organism is *Arthrinium arundinis* (Corda) Dyko & Sutton (MF 6175, ATCC 74359) which was isolated from an abandoned bird's nest collected in El Chayote Protected Area, Province of Alajuela, Costa Rica. *Arthrinium arundinis* is a widely distributed fungus, common on decaying grasses and other plant materials. In the mycological literature, this fungus is commonly referred to as the Arthrinium state of *Apiospora montagnei* Saccardo.

In agar culture, colonies of the fungus exhibit the following morphology:

Colonies on Emerson's YpSs agar (Difco) at 25° C., 12 hr photoperiod attaining 22–24 mm in 14 days, slight raised, with advancing zone appressed to submerged, even t0 irregular, with patchy, irregular floccose aerial mycelium, dull, obscurely zonate, at first transluscent, but soon pale translucent gray, mottled pale gray to dark olivaceous gray or olivaceous brown, Olive Gray, Dresden Brown, Isabella Color, Old Gold, Light Brownish Olive, (capitalized color names from Ridgway, R. 1912 Color Standards and Nomenclature. Published by the author, Washington, D.C.), with reverse yellow, Light Chalcedony Yellow to dull gray, exudates absent.

Colonies on cornmeal agar (Difco) at 25° C., 12 hr photoperiod attaining 25–28 mm in 14 days, submerged to appressed at the margin, raised towards the center, with scant aerial mycelium, granular to pulverulent when sporulating, transluscent to gray or dark gray, reverse transluscent to pale gray, exudates absent.

Colonies on YM agar (Difco) at 25° C., 12 hr photoperiod attaining 24–30 mm in 14 days, raised, velvety to lanose, with some radial sectoring, obscurely zonate, with margin even and submerged, mostly white, later pale gray to grayish brown, similar to color on YpSs agar, reverse translucent to pale brownish gray or olivaceous gray, exudates absent. No growth at 37° C. on YM.

Conidiophores extremely short, up to 8 μm long, hyaline, integrated, arising as lateral or terminal branches from main hyphal axes, 1–3 celled, often with spherical to pyriform, inflated basal cells with give rise to short filamentous terminal cells that are tapered apically toward conidiogenous locus, solitary to densely aggregated, collapsing soon after condium formation. Conidiogenous cells arising from inflated basal cells, holoblastic, basauxic, hyaline, thin-walled, filamentous or tapered apically. Conidia lenticular, circular to pyriform in face view, compressed in side view, smooth, yellowish brown, often with pale band along compressed edge, 6–8 μm in diameter. When MF 6175 is inoculated onto autoclaved banana leaves supported by cornmeal agar, conidia are strongly aggregated into pustules that could be interpreted to be sporodochia or acervuli.

MF 6175 is readily assigned to the anamorph genus Arthrinium based on its dark, lenticular conidia borne on short, filamentous conidiogenous cells, and lack of setae, stroma or ascomata. From about 20 described species of Arthrinium, A. arundinis is distinguished by its smooth, round, lenticular conidia which smaller that most other species of the genus and thin, filamentous, hyaline conidiogenous cells.

Although the invention is discussed principally with respect to the specific strain, it is well known in the art that the properties of microorganisms can be varied naturally and artificially. Thus, all strains derived from Arthrinium arundinis MF 6175, ATCC 74359 including varieties and mutants, whether obtained by natural selection, produced by the action of mutating agents such as ionizing radiation or ultraviolet irradiation, or by the action of chemical mutagens such as nitrosoguanidine, are contemplated to be within the scope of this invention.

The production of the compound may be carded out by cultivating Arthrinium arundinis MF 6175, ATCC 74359 in a suitable nutrient medium under conditions described herein until a substantial amount of antifungal activity is detected in the fermentation broth, harvesting by extracting the active components from the mycelial growth with a suitable solvent, concentrating the solution containing the desired component, then subjecting the concentrated material to chromatographic separation to isolate the compound from other metabolites also present in the cultivation medium.

Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium. Certain carbon sources are preferred as hereinafter set forth.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extract, corn steep liquors, distillers solubles, cottonseed meal, meat extract, and the like. The various sources of nitrogen can be used alone or in combination in amounts ranging from 0.05 to 5 percent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Representative suitable solid and liquid production media may be seen in the tables which follow. Also included is a representative seed medium. These, however, are merely illustrative of the wide variety of media which may be employed and are not intended to be limiting.

TABLE 1

| KF SEED MEDIUM | | Trace Element Mix | |
| --- | --- | --- | --- |
| | per liter | | per liter |
| Corn Steep Liquor | 5 g | FeSO$_4$.7H$_2$O | 1 g |
| Tomato Paste | 40 g | MnSO$_4$.4H$_2$O | 1 g |
| Oat flour | 10 g | CuCl$_2$.2H$_2$O | 25 mg |
| Glucose | 10 g | CaCl$_2$ | 100 mg |
| Trace Element Mix | 10 ml | H$_3$BO$_3$ | 56 mg |
| | | (NH$_4$)$_6$Mo$_7$O$_{24}$.4H$_2$O | 19 mg |
| | | ZnSO$_4$.7H$_2$O | 200 mg | pH = 6.8

TABLE 2

| LIQUID PRODUCTION MEDIUM | |
| --- | --- |
| Component | per liter |
| Maltose | 75 g |
| V-8 Juice | 200 ml |
| Soy Flour | 1 g |
| L-Proline | 3 g |
| MES* | 16.2 g | pH adjusted to 6.5 with NaOH before autoclaving
*-2-(N-morpholino)-ethanesulfonic acid The liquid production medium was found to give the best yield of the compound. In the production of the compound, generally, the culture is first grown in a seed medium and the culture growth then used to inoculate a production medium. The production medium may be a solid medium or a liquid medium.

In carrying out the production of Compound I, vegetative mycelia of the culture were prepared by inoculating 54 ml of seed medium (Table 1) in a 250 ml unbaffled Erlenmeyer flask with 2 ml of mycelia in 10% glycerol that had been stored at −80° C. Seed cultures were incubated for 3 days at 25° C. and 85% relative humidity on a rotary shaker with a 5-cm throw at 220 rpm in a room with constant fluorescent light. Two ml portions of the culture were used to inoculate a second stage seed culture and further incubated for 3 days with the conditions noted above. Two ml portions of this 3 day culture were used to inoculate 50 ml portions of liquid production medium (Table 2) in 250 ml unbaffled Erlenmeyer flasks. All other incubation parameters remained the same as stated above. Maximal production of the compound occurred between days 14 and 21. At harvest, the compound was extracted from the mycelial growth with equal volume of either methanol or methyl ethyl ketone followed by shaking with the solvent at 220 rpm for 1 hour at 25° C. The samples were centrifuged for 20 minutes at 3000 rpm to obtain a clear extract.

The usefulness of the compound as an antifungal agent, especially as an antimycotic agent, may be demonstrated with the compound in a broth microdilution assay for the determination of minimum inhibitory concentration (MIC) and minimum fungicidal concentration (MFC) against fungi. The compound is found to be effective in the assay against a panel of fungi selected for their resistance/susceptibility to known compounds, animal virulence, source and clinical importance, at concentrations comparable to an established antifungal agent, amphotericin B.

In the microbroth dilution assay, microorganisms were selected by streaking a yeast culture on Sabouraud dextrose agar (SDA) and incubating for 24–48 hours at 35°–37° C. Three to five characteristic colonies were selected and transferred to a fresh plate and incubated under similar conditions. From the regrowth, 3 to 5 colonies were selected and suspended in 10 milliliters of YM broth (Difco) and incubated for 4 hours at 35°–37° C. shaking at 225 rpm. The 4 hour broth cultures were adjusted optically to 86% transmission resulting in a concentration of $1-5\times10^6$ cfu/ml which was further diluted 1:100 in YNBD (yeast nitrogen base with 1% dextrose) to obtain a concentration of $1-5\times10^4$ cfu/ml for use as inocula.

The test compound was dissolved at 256 µg/ml in 10% DMSO and diluted 2× into the first well to achieve a concentration of 256 µg/ml at 5% DMSO in the first well. Compounds are subsequently serially diluted 2× and cell suspension is added to each well resulting in an additional 2× dilution of compound. 75 µl of said solution is delivered to each well in colunto 1 of a 96-well, U-bottomed plate. The compounds in column 1 were then serially diluted two-fold to yield concentrations from 128 µg/ml to 0.03 µg/ml.

Amphotericin B, the control compound, was prepared as a stock solution of 256 µg/ml in 10% DMSO and 75 µl of said solution delivered to colmnn 1 of a 96-well, U-bottomed plate. The compounds in column 1 were then serially diluted two-fold to yield concentrations from 128 µg/ml to 0.03 µg/ml.

The plates containing the diluted compounds were then inoculated with 75 µl/well of the appropriate microorganism and incubated for 48 hours at 35°–37° C. with MIC (minimum inhibitory concentration) determinations carded out after 24 hours of incubation (except Cryptococcus strains which are read at 48 hours). Growth and sterility controls for each organism and sterility checks for the compounds also were carried out.

After recording M/Cs at 24 hours, the microtiter plates were shaken gently to resuspend the cells. A 1.5 µl sample was transferred from each well of the 96-well plate to a single reservoir inoculum plate containing SDA. The inoculated SDA and corresponding microtiter plates were incubated for 24 hours at 35°–37° C. For Cryptococcus neoformans, SDA plates were inoculated at 48 hours after recording MICs and incubated 48 hours before reading the MFG. MFC is the lowest concentration of compound at which either no growth or growth of $\leq 4$ colonies occur.

No MFC values are indicated for Aspergillus fumigatus since colony counts are unreliable with filamentous species. Instead, a Minimum Effective Concentration (MEG) is reported. The MEC is defined as the lowest concentration of drug which effects a severe morphological change in the cells. The MEC is scored macroscopically by direct observation of the plate wells after 24 hours and reflects microscopic alterations in cell morphology (Kurtz et al. AAC 1994 38:1480–1489).

| Minimum Fungicidal Concentration (MFC) Minimum Inhibitory Concentration (MIC) µg/ml | | | |
|---|---|---|---|
| Strain | MIC | MFC | MEC |
| Candida albicans (MY1055) | 4.0 | 4.0 | |
| Candida glabrata (MY1381) | 2.0 | 1.0 | |
| Candida parapsilosis (MY1010) | 4.0 | 2.0 | |
| Candida pseudotropicalis (MY2099) | 8.0 | 8.0 | |
| Candida tropicalis (MY1124) | 8.0 | 8.0 | |
| Candida albicans (CLY539) | 2.0 | 2.0 | |
| Candida albicans (CA2) | 16.0 | 16.0 | |
| Candida tropicalis (MY1012) | 16.0 | 16.0 | |
| Candida guillermondii (MY1019) | 64.0 | 64.0 | |
| Candida krusei | 4.0 | 2.0 | |
| Cryptococcus neoformans (MY2061) | >64.0 | 32.0 | |
| Cryptococcus neoformans (MY2062) | 32.0 | 64.0 | |
| Saccharomyces cerevisiae (MY2140) | 8.0 | 8.0 | |
| Aspergillus fumigatus (MY4839) | >64.0 | | 0.5 |
| Aspergillus fumigatus (MY5668) | 64.0 | | 1.0 |

The compound is also useful for inhibiting the growth of filamentous fungi. Such use may be illustrated in the following tests with Aspergillus flavus, Fusarium oxysporum, Ustilago zeae and the like.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

The samples to be tested for production of antifungal agent are applied directly to the agar plates as methanol solutions. When the sample to be tested is crude broth, it may be centrifuged prior to application. The assay plates are then incubated at either 28° C. or 37° C. for 24 hours. Following incubation, the inhibition zones are measured. Effects on growth are also noted as to appearance. The compound is seen to effectively inhibit growth of the fungal organisms.

In view of the broad spectrum of activity, the product of the present invention either singly or as a mixture is adaptable to being utilized in various applications of antifungal compositions. In such case, compounds may be admixed with a biologically inert carrier, generally with the aid of a surface active dispersing agent, the nature of which would vary depending on whether the use is for the control of pathogens infecting man or animals, or for control of fungi in agriculture such as in soil or plant parts, or for the control of fungi in inanimate objects.

In compositions for medical applications, the compound may be admixed with a pharmaceutically acceptable carrier, the nature of which will depend on whether the composition is to be topical, parenteral or oral.

If said application is to be topical, the drag may be formulated in conventional creams and ointments such as white petrolatum, anhydrous tanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by mixing the component drugs with any of the usual pharmaceutical media, including for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricants such as calcium stearate, together with binders, disintegrating agents and the like.

These compositions are then administered in amounts sufficient to obtain the desired antifangal effect. For medical applications, the method comprises administering to a subject in need of treatment a therapeutically effective antifungal amount of the compounds. The appropriate dose will vary depending on age, severity, body weight and other conditions. For topical application, the compositions are applied directly to the area where control is desired. For internal administration, the composition may be applied by injection or may be administered orally.

For non-medical application, the product of the present invention, either alone or as a mixture, may be employed in compositions in an inert carrier which included finely divided dry or liquid diluents, extenders, fillers, conditioners and excipients, including various clays, diatomaceous earth, talc, and the like or water and various organic liquids such as lower alkanols, such as ethanol and isopropanol, or kerosene, benzene, toluene and other petroleum distillate fractions or mixtures thereof.

The following example illustrates the invention but is not to be construed as limiting the invention disclosed herein.

EXAMPLE I (I)

Isolation

A methanol (MeOH) extract of a liquid fermentation of *Arthrinium arundinis* MF 6175, corresponding to 600 ml of whole broth was filtered, concentrated to dryness and partitioned between methyl ethyl ketone (MEK) and water. The MEK layer was dried, reconstituted in MeOH/$H_2O$ and chromatographed on an open Amicon C8 reverse phase colunto using a MeOH/$H_2O$ step gradient. The rich cut from the open reverse phase column was further purified on a preparative DuPont Zorbax C8RX HPLC colunto which yielded 62 mg of the compound upon concentration.

Compound I has the spectral properties previously described.

The following examples illustrate representative compositions containing Compound I.

EXAMPLE A 1000 compressed tablets each containing 500 milligrams of Compound I are prepared from the following formulation:

|  | Grams |
| --- | --- |
| Compound I | 500 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 500 milligrams of Compound I are prepared from the following formulation:

| Compound I | 500 |
| --- | --- |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C 250 milliliters of an injectible solution are prepared by conventional procedures from the following formulation:

| Dextrose | 12.5 grams |
| --- | --- |
| Water | 250 milliliters |
| Compound I | 400 milligrams |

The ingredients are blended and sterilized for use.

EXAMPLE D

An ointment suitable for topical application may be prepared by intimately dispersing 13 mg of Compound I in 1 g of commercially available polyethylene/hydrocarbon gel.

EXAMPLE E

An aerosol composition may be prepared having the following formulation (per canister):

| Compound I | 24 mg |
| --- | --- |
| Lecithin NF, liquid concentrate | 1.2 mg |
| Trichlorofluoromethane | 4.025 g |
| Dichlorodefluoromethane | 12.15 g |

What is claimed is:
1. A compound having the structure:

(I)

2. An antifungal composition comprising an antifungally effective amount of the compound of claim 1 in admixture with a biologically inert carrier or diluent.

3. A composition according to claim 2 wherein the carrier is a pharmaceutically acceptable carrier.

4. A method for controlling fungal growth which comprises administering to the site where growth is to be controlled, an antifungally effective amount of the compound of claim 1.

5. A method for combatting fungal infections in mammals which comprises administering to a region of the animal afflicted with said fungi a therapeutically effective amount of the compound of claim 1.

6. A process for producing the compound of claim 1 which comprises aerobically cultivating *Arthrinium arundinis* ATCC 74359 in a nutrient medium containing assimilable sources of carbon and nitrogen and isolating said compound therefrom.

* * * * *